US007740696B2

(12) United States Patent
Takahashi et al.

(10) Patent No.: US 7,740,696 B2
(45) Date of Patent: Jun. 22, 2010

(54) WATER-SOLUBLE AZO COMPOUND, INK COMPOSITION, AND COLORED ARTICLE

(75) Inventors: Shinjiro Takahashi, Kita-ku (JP); Yoshiyuki Dejima, Kita-ku (JP); Yasuo Shirasaki, Saitama (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 292 days.

(21) Appl. No.: 12/083,536

(22) PCT Filed: Dec. 28, 2005

(86) PCT No.: PCT/JP2005/024117

§ 371 (c)(1),
(2), (4) Date: Apr. 14, 2008

(87) PCT Pub. No.: WO2007/049366

PCT Pub. Date: May 3, 2007

(65) Prior Publication Data

US 2009/0117341 A1    May 7, 2009

(30) Foreign Application Priority Data

Oct. 25, 2005   (JP)   ............... 2005-310471

(51) Int. Cl.
*C09D 11/02*   (2006.01)
*C09B 33/12*   (2006.01)
*B41J 2/01*    (2006.01)

(52) U.S. Cl. .................. 106/31.48; 534/797; 347/100

(58) Field of Classification Search ............. 106/31.48; 534/797; 347/100; 428/195.1
See application file for complete search history.

(56) References Cited

U.S. PATENT DOCUMENTS

| 3,945,990 | A | * | 3/1976 | Ikeda et al. | .................. | 534/797 |
| 5,268,459 | A | | 12/1993 | Gregory et al. | ............. | 534/758 |
| 5,374,301 | A | | 12/1994 | Gregory et al. | .......... | 106/31.48 |
| 5,519,121 | A | * | 5/1996 | Renner et al. | ............ | 106/31.48 |
| 5,622,550 | A | | 4/1997 | Konishi et al. | ............ | 106/31.48 |
| 5,631,352 | A | | 5/1997 | Lauk | .......................... | 534/797 |
| 6,290,763 | B1 | | 9/2001 | Millard et al. | ............ | 106/31.48 |
| 6,867,286 | B1 | * | 3/2005 | Holloway et al. | ........... | 534/797 |
| 7,029,503 | B2 | * | 4/2006 | Odani et al. | .................... | 8/549 |
| 7,056,374 | B2 | * | 6/2006 | Kitayama et al. | ........ | 106/31.48 |
| 7,150,783 | B2 | * | 12/2006 | Oshaughnessy et al. | .. | 106/31.48 |
| 7,163,576 | B2 | * | 1/2007 | Oshaughnessy et al. | .. | 106/31.48 |
| 7,387,668 | B2 | * | 6/2008 | Kitayama et al. | ........ | 106/31.48 |
| 7,553,358 | B2 | * | 6/2009 | Okamura et al. | ......... | 106/31.48 |
| 2004/0068102 | A1 | | 4/2004 | Holloway et al. | ........... | 534/632 |
| 2005/0115458 | A1 | * | 6/2005 | Oki et al. | ................. | 106/31.48 |
| 2006/0005744 | A1 | * | 1/2006 | Kitayama et al. | ........ | 106/31.48 |
| 2008/0274285 | A1 | * | 11/2008 | Okamura et al. | ......... | 106/31.48 |
| 2009/0117341 | A1 | | 5/2009 | Takahashi et al. | ........ | 428/195.1 |
| 2009/0130399 | A1 | | 5/2009 | Takahashi et al. | ........ | 428/195.1 |
| 2010/0068475 | A1 | * | 3/2010 | Morita et al. | ............ | 106/31.48 |

FOREIGN PATENT DOCUMENTS

| GB | 595181 | 11/1947 |
| JP | 55-135166 | 10/1980 |
| JP | 4-233975 | 8/1992 |
| JP | 8-3469 | 1/1996 |
| JP | 8-325493 | 12/1996 |
| JP | 2005-298636 | 10/2005 |
| JP | 2006-152244 | 6/2006 |
| JP | 2008-13667 | 1/2008 |
| JP | 2008-56830 | 3/2008 |
| JP | 2008-88281 | 4/2008 |
| JP | 2008-88282 | 4/2008 |
| WO | 98/12263 | 3/1998 |
| WO | 2004/007619 | 1/2004 |
| WO | 2007/049366 | 5/2007 |

OTHER PUBLICATIONS

The International Search Report dated Mar. 20, 2006.
The International Search Report dated Jul. 29, 2008 in co-pending U.S. Appl. No. 12/451,071.
The International Search Report dated Mar. 20, 2006 (PCT/JP2006/301059; in co-pending U.S. Appl. No. 11/990,210).
The International Search Report dated Dec. 4, 2007 (PCT/JP2007/070809; in co-pending U.S. Appl. No. 12/312,113).

* cited by examiner

*Primary Examiner*—Helene Klemanski
(74) *Attorney, Agent, or Firm*—Nields, Lemack & Frame, LLC

(57) ABSTRACT

The present invention relates to a water-soluble azo compound for yellow represented by the following formula (1)

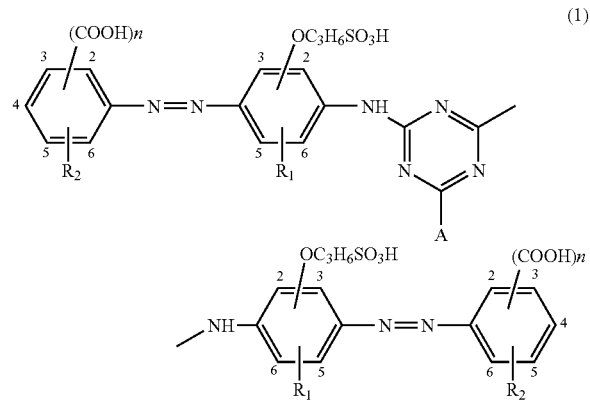

wherein, A represents a hydroxy group, a morpholino group, an amino group, an aliphatic amine residue which may have a substituent, an aromatic amine residue which may have a substituent, a phenoxy group which may have a substituent, or an alkoxy group which may have a substituent, $R_1$ represents a hydrogen atom or an alkyl group having 1 to 4 carbon atoms, $R_2$ represents a hydrogen atom, a nitro group or a hydroxy group, and n represents an integer number of 1 to 3, respectively as a free acid, and an ink composition containing the same; said ink composition has good stability and is suitable for inkjet printing; and printed matters therewith have very high fastness such as ozone fastness and the like.

19 Claims, No Drawings

WATER-SOLUBLE AZO COMPOUND, INK COMPOSITION, AND COLORED ARTICLE

TECHNICAL FIELD

The present invention relates to an azo compound and use thereof. More specifically, the present invention relates to a water-soluble azo compound, an ink composition containing the same and a colored article colored therewith.

BACKGROUND ART

In the recording method by means of an ink jet printer which is one of typical methods among various color recording methods, various methods for discharging ink have been developed, where ink droplets are generated and adhered onto various record-receiving materials (such as paper, film and cloth) to perform recording. This method has been rapidly prevailing lately and is expected to continue growing remarkably in the future because of such features as quietness without noise generation due to no direct contact of a recording head with a record-receiving material and as easiness in downsizing, speedup and colorization. Conventionally, as an ink for fountain pens, felt-tip pens or the like and an ink for inkjet recording, inks by dissolving a water-soluble dye in an aqueous medium have been used, and in these water-soluble inks, a water-soluble organic solvent is generally added to prevent ink from clogging at a pen tip or an inkjet nozzle. These inks are required to provide recorded images with sufficient density, not to clog at a pen tip or an inkjet nozzle, to dry quickly on record-receiving materials, to bleed less, to have good storage stability and so on. In addition, recorded images formed are required to have fastnesses such as excellent water fastness, moisture fastness, light fastness and gas fastness.

Meanwhile, images or character information on color displays of computers are generally expressed by subtractive color mixing of 4 color inks of yellow (Y), magenta (M), cyan (C) and black (K) for color recording by an ink jet printer. In order to reproduce, as faithfully as possible, images expressed by additive color mixing of red (R), green (G) and blue (B) on CRT (cathode ray tube) displays and the like, through images by subtractive color mixing, it is desired that coloring matters to be used for ink, especially Y, M and C, respectively have hues close to their standards and vividness. In addition, it is required that inks are stable in storage for a long period of time, and images printed as mentioned above have a high concentration and are excellent in fastnesses such as water fastness, moisture fastness, light fastness, and gas fastness. The gas fastness here means durability against the phenomenon that oxidizing gases such as nitrogen oxide gas and ozone gas having oxidizing effect, which exist in the air, react with a coloring matter (dye) on or in recording paper having recorded images to incur discoloration or fading of printed images. In particular, the ozone gas is regarded as a main causative substance to promote the phenomenon of discoloration of inkjet recorded images. As this phenomenon of discoloration or fading is characteristics of inkjet images, improvement of ozone gas fastness is an important technical challenge in this field. In particular, porous white inorganic substance is used for many of ink receiving layers provided on the surfaces of inkjet professional paper to obtain photo quality in order to dry ink sooner and to make bleeding less in high image quality, resulting in that on such recording paper, discoloration or fading by the ozone gas is noticeably observed. Along with recent diffusion of digital cameras and color printers, there are more opportunities to print images obtained using digital cameras and the like at home, and fading of images caused by oxidizing gases in the air during storage of printed materials obtained is often considered as a problem.

As an example of the compounds with excellent water-solubility and vividness which has been conventionally used as a yellow coloring matter for inkjet, C.I. (color index) Direct Yellow 132 can be cited (for example, see Patent Literatures 1 to 3).
[Patent Literature 1] JP H11-70729 A
[Patent Literature 2] JP 2000-154344 A, Examples A1 to 5
[Patent Literature 3] JP 2003-34763 A, Page 11, Example 4

DISCLOSURE OF THE INVENTION

Problems to be Solved by the Invention

Not all of the hue, vividness, light fastness, water fastness, moisture fastness, gas fastness and dissolving stability in C.I. (color index) Direct Yellow 132 are satisfactory for use, and development of yellow coloring matter with further improvement on these fastnesses has been required.

The present invention has an object to provide a water-soluble yellow coloring matter (compound) which has high solubility in water, and hue and vividness suitable for inkjet recording and gives good water fastness, moisture fastness, light fastness and gas fastness to recorded articles, and an ink composition comprising it.

Means of Solving the Problems

The inventors of the present invention intensively studied a way to solve the above problems and have found that a water-soluble disazo compound represented by a specific formula and an ink composition comprising it can solve the above problems, and completed the present invention.

That is, the present invention relates to;
(1) A water-soluble azo compound represented by the following formula (1)
(1)

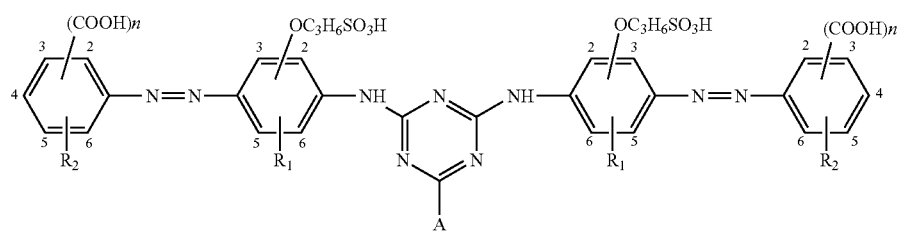

[KA 1]

(wherein, A represents a hydroxy group, an amino group, a morpholino group, an aliphatic amine residue which may have a substituent, an aromatic amine residue which may have a substituent, a phenoxy group which may have a substituent or an alkoxy group which may have a substituent, $R_1$ represents a hydrogen atom or an alkyl group having 1 to 4 carbon atoms, $R_2$ represents a hydrogen atom, a nitro group or a hydroxy group, n represents an integer number of 1 to 3, respectively) as free acid, (2) The water-soluble azo compound according to (1), wherein $R_1$ in the formula (1) is a hydrogen atom, (3) The water-soluble azo compound according to (1) or (2), wherein $R_2$ in the formula (1) is a hydrogen atom, (4) The water-soluble azo compound according to any one of (1) to (3), wherein A in the formula (1) is a group represented by the following formula (2) or (3)

[KA 2]

—NHC$_2$H$_4$SO$_3$H    (2)

—NHCH$_2$COOH    (3)

or a hydroxy group, (5) An ink composition characterized by comprising the water-soluble azo compound according to any one of (1) to (4), (6) The ink composition according to (5), comprising a water-soluble organic solvent, (7) The ink composition according to (5) or (6), which is for inkjet recording, (8) An inkjet recording method characterized by using the ink composition according to any one of (5) to (7) as an ink in an inkjet recording method where ink droplets are discharged responding to recording signals to perform recording on a record-receiving material, (9) The inkjet recording method according to (8), wherein the record-receiving material is a communication sheet,

(10) The inkjet recording method according to (9), wherein the communication sheet is a sheet having an ink receiving layer comprising a porous white inorganic substance,

(11) A colored article colored with the water-soluble azo compound according to any one of (1) to (4) or the ink composition according to any one of (5) to (7),

(12) The colored article according to (11), wherein coloring is performed by an ink jet printer,

(13) An ink jet printer loaded with a container containing the ink composition according to any one of (5) to (7),

(14) The water-soluble azo compound according to (1), wherein in the formula (1), n is 1 or 2, A is a hydroxy group, an amino group, a morpholino group, a C1 to C4 alkylamino group having a hydroxy group, a sulfo group or a carboxy group as a substituent, an anilino group substituted by a mono- or di-carboxy group, or a phenoxy group, and —OC$_3$H$_6$SO$_3$H is substituted on the 3-position to the azo group,

(15) The water-soluble azo compound according to (1), wherein (COOH)n in the formula (1) is substituted at the 3-position or the 4-position when n=1, and at the 3-position and the 5-position when n=2,

(16) The water-soluble azo compound according to (1), wherein $R_1$ in the formula (1) is a hydrogen atom, and (COOH)n is substituted at the 3-position or the 4-position when n=1, and at the 3-position and the 5-position when n=2,

(17) The water-soluble azo compound according to claim 1, wherein A in the formula (1) is a hydroxy group or a C1 to C4 alkylamino group having a sulfo group or a carboxy group as a substituent, $R_1$ is a hydrogen atom, (COOH)n is substituted at the 3-position or the 4-position when n=1, and at the 3-position and the 5-position when n=2,

(18) The water-soluble azo compound according to (17), wherein A in the formula (1) is a sulfoethylamino group or a carboxy methylamino group, $R_2$ is a hydrogen atom, n=2 and the substitution positions of the two carboxy groups are the 3-position and the 5-position,

(19) A yellow coloring matter comprising the compound of the formula (1).

Effect of the Invention

The water-soluble azo compound represented by the formula (1) of the present invention or a salt thereof (hereinafter, referred to as water-soluble azo compound for short, including a salt thereof) is excellent in solubility in water, has a characteristic that in the process of producing the ink composition, for example, filterability through a membrane filter is good, and provides yellow hue which is very vivid on inkjet recording paper and high in lightness. In addition, the ink composition comprising this compound doesn't exhibit crystal precipitation, change in physical property, change in hue, nor the like after storage for a long period of time, and exhibits good storage stability. Further, printed articles by using this ink composition as an ink for inkjet recording have ideal hue as yellow hue without selecting the record-receiving material (paper, film or the like), and this ink composition can make it possible to faithfully reproduce photo-like color images on paper. Furthermore, this ink composition can give good fastnesses such as good water fastness, moisture fastness, light fastness and gas fastness to the recorded articles where the record carried out on the record-receiving material having surfaces coated with a porous white inorganic substance like inkjet professional paper (film) for photo quality and excellent stability in storage for a long period of time to photo-like recorded images. Thus, the water-soluble azo compound of the formula (1) is extremely useful for ink, especially as a yellow coloring matter for ink for inkjet recording.

BEST MODE FOR CARRYING OUT THE INVENTION

The present invention will be explained more specifically. In this connection, a sulfo group and a carboxy group are shown in the free acid form unless otherwise specified hereinafter.

Preferable alkyl, alkoxy or the like includes C1 to C4 alkyl or C1 to C4 alkoxy unless otherwise specifically noted in the present invention.

The water-soluble azo compound of the present invention is represented by the following formula (1).

[KA 3]

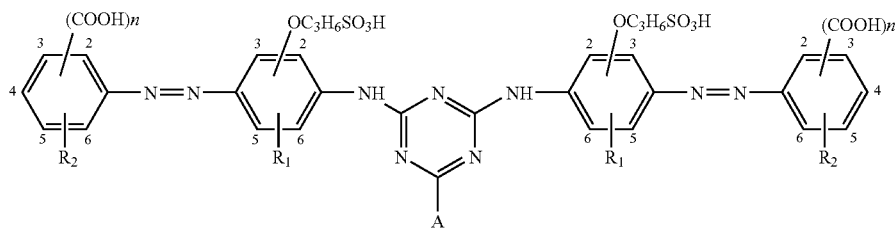

(1)

In the formula (1), A represents a hydroxy group, an amino group, a morpholino group, an aliphatic amine residue which may have a substituent, an aromatic amine residue which may have a substituent, a phenoxy group which may have a substituent or an alkoxy group which may have a substituent.

The substituent of the above aliphatic amine residue which may have a substituent is preferably a sulfo group, a carboxy group or a hydroxy group, and more preferably a sulfo group or a carboxy group.

Preferable aliphatic groups include a C1 to C4 alkyl group.

Specific examples of the aliphatic amine residue which may have a substituent include a C1 to C4 alkylamino group having a sulfo group, a carboxy group or a hydroxy group as a substituent, for example, a 2-sulfoethylamino group, a carboxymethylamino group, a 2-hydroxyethylamino group, a 2-carboxyethylamino group, a 1-carboxyethylamino group, a 1,2-dicarboxyethylamino group, a di(carboxymethyl)amino group and the like. Among them, a 2-sulfoethylamino group or a carboxymethylamino group is more preferable.

And, preferable substituents of the above aromatic amine residue which may have a substituent are a carboxy group and a sulfo group. Specific examples of the aromatic amine residue which may have a substituent include an anilino group, a 3,5-dicarboxyanilino group, a 4-sulfoanilino group and the like.

Further, preferable substituents of the phenoxy group which may have a substituent are a sulfo group, a carboxy group, a C1 to C4 acyl group and a hydroxy group. Specific examples of the phenoxy group which may have a substituent include a phenoxy group, a 4-sulfophenoxy group, a 4-carboxyphenoxy group, a 4-acetylaminophenoxy group, a 4-hydroxyphenoxy group and the like.

Furthermore, preferable substituents of the alkoxy group which may have a substituent are a hydroxy group and a carboxy group. Specific examples of the alkoxy group which may have a substituent include a methoxyethoxy group, a hydroxyethoxy group, a 3-carboxypropoxy group and the like, respectively.

Among them, A is preferably a morpholino group, a hydroxy group, or an aliphatic amine residue (preferably a C1 to C4 alkylamino group) which may have a group, as a substituent, selected from the group consisting of a sulfo group, a carboxy group and a hydroxy group, more preferably a sulfoethylamino group, a carboxymethylamino group, a morpholino group and a hydroxy group, and particularly preferably a sulfoethylamino group or a carboxymethylamino group.

$R_1$ represents a hydrogen atom or an alkyl group having 1 to 4 carbon atoms, and specific examples of the alkyl group having 1 to 4 carbon atoms include a methyl group, an ethyl group, an n-propyl group, an iso-propyl group, an n-butyl group, an iso-butyl group, a sec-butyl group, a tert-butyl group and the like. Among them, $R_1$ is preferably a hydrogen atom.

$R_2$ represents a hydrogen atom, a nitro group, a halogen atom or a hydroxy group. Among them, $R_2$ is preferably a hydrogen atom.

The substitution position of the sulfopropoxy group on the benzene ring having substituent $R_1$ is preferably the 2-position or the 3-position to the substitution position of the azo group on this benzene ring, and more preferably the 3-position.

n represents an integer number of 1 to 3, and preferably 1 or 2. In this connection, the substitution position of the carboxy group on the benzene ring is preferably the 2-position, the 3-position or the 4-position when n=1, and the 3-position and the 5-position when n=2.

For the water-soluble azo compound represented by the formula (1) of the present invention, the compound represented by the following formula (4) can be cited as a preferable compound. In the formula (4), $A_1$ represents a 2-sulfoethylamino group, a carboxymethylamino group or a hydroxy group and m represents 1 or 2, respectively. In addition, in the formula (4), the carboxy group on the benzene ring is bonded to the 3-position or the 4-position, preferably the 3-position (when m=1), or to the 3-position and the 5-position (when m=2), respectively.

(4)

[KA 4]

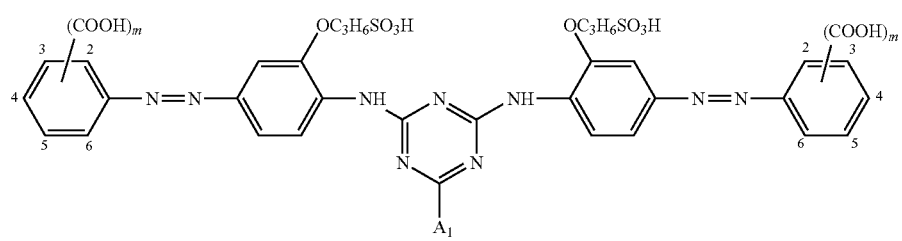

The compound of the formula (1) can form a salt structure with an inorganic or organic cation. Examples of the salt with an inorganic ion include a salt with a lithium ion, a salt with a sodium ion, a salt with a potassium ion (an alkali metal salt) and the like. In addition, an example of the salt with an organic cation includes a salt with an ammonium ion represented by the formula (5).

[KA 5]

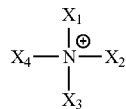

(5)

(wherein, each of $X_1$ to $X_4$ independently represents a hydrogen atom, an alkyl group, a hydroxyalkyl group or a hydroxyalkoxyalkyl group)

In the above, examples of the alkyl group for $X_1$ to $X_4$ include a C1 to C4 alkyl group, for example, a methyl group, an ethyl group and the like, and similarly examples of the hydroxyalkyl group include a hydroxy C1 to C4 alkyl group, for example, a hydroxymethyl group, a hydroxyethyl group, a 3-hydroxypropyl group, a 2-hydroxypropyl group, a 4-hydroxybutyl group, a 3-hydroxybutyl group, a 2-hydroxybutyl group and the like, and in addition, examples of the hydroxyalkoxyalkyl group include a hydroxyethoxymethyl group, a 2-hydroxyethoxyethyl group, a 3-(hydroxyethoxy)propyl group, a 3-(hydroxyethoxy)butyl group, a 2-(hydroxyethoxy) butyl group and the like. Preferable ammonium ion of the formula (5) can include a C1 to C4 alkylammonium ion which may have a group, as a substituent, selected from the group consisting of a hydroxy group, a C1 to C4 alkoxy group and a hydroxy C1 to C4 alkoxy group.

Preferable salts among the above salts include a sodium salt, a potassium salt, a lithium salt, a monoethanolamine salt, a diethanolamine salt, a triethanolamine salt, a monoisopropanolamine salt, a diisopropanolamine salt, a triisopropanolamine salt, an ammonium salt and the like. Among them, particularly preferable are a lithium salt and a sodium salt.

The salt of the compound of the formula (1) described above can be easily obtained by the following method and the like.

For example, a sodium chloride can be added to a reaction solution before adding methanol in Example 1 described later or to the water dissolving a wet cake or its dried one or the like containing a compound of the formula (1), for salting out followed by filtration to obtain a sodium salt of the compound of the formula (1) as a wet cake.

Further, the obtained wet cake of sodium salt can be dissolved in water and then hydrochloric acid is added thereto to accordingly adjust the pH, for example, to no more than 1 or from weakly acidic to near-neutral so as to obtain a solid, which is then filtered to obtain free acid of the compound of the formula (1), or a mixture where some of the compound of the formula (1) is sodium salt and some of the compound of the formula (1) is free acid, respectively.

Furthermore, while stirring the wet cake of free acid of the compound of the formula (1) together with water, for example, a potassium hydroxide, a lithium hydroxide, ammonia water, a hydroxide of the formula (5) or the like can be added thereto to make it alkaline so as to obtain a corresponding potassium salt, lithium salt, ammonium salt or quaternary ammonium salt, respectively.

Among these salts, particularly preferable are a lithium salt and a sodium salt as describe above.

The water-soluble azo compound represented by the formula (1) of the present invention can be produced, for example, as follows.

That is, for example, the compound of the following formula (A) (a sulfopropoxy-substituted anilines which may have a substituent) obtained by referring to the examples described in JP 2004-75719 A is converted to a methyl-ω-sulfonic acid derivative (B) using a sodium bisulfite and a formalin. Subsequently, in the conventional manner, an aromatic amine represented by the following formula (C) (a carboxy-substituted anilines which may have a substituent) is diazotized and subjected to coupling reaction with the above obtained methyl-ω-sulfonic acid derivative of the formula (B) at 0 to 5° C. and pH 0 to 2, followed by carrying out hydrolyzation reaction at 60 to 80° C. and pH 10.5 to 11.0 to obtain an azo compound having an amino group represented by the following formula (D).

Next, 2 equivalent amount of the obtained azo compound represented by the formula (D) and 1 equivalent amount of a cyanuric halide, for example a cyanuric chloride, are condensed at a temperature of 20 to 25° C. at weakly acidic (typically at pH 5 to 6) to obtain a condensate represented by the formula (E).

Further, in the obtained formula (E), a chlorine atom substituted at the position corresponding to A in the formula (1) is condensed under the conditions of a temperature of 75 to 80° C. and pH 7 to 8 to be substituted by a group A, for example, a hydroxide ion, ammonia, morpholine, aliphatic amine which may have a substituent, aromatic amine which may have a substituent, phenol which may have a substituent, alcohol which may have a substituent or the like so as to obtain a water-soluble azo compound represented by the formula (1) of the present invention.

Specific examples of the compound of the following formula (A) include, for example, 2-sulfopropoxyaniline (a compound where $R_1$=a hydrogen atom in the formula (A)), 2-sulfopropoxy-5-methylaniline (a compound where $R_1$=methyl in the formula (A)) and the like.

Specific examples of the compound of the following formula (C) include, for example, commercially available 3-aminobenzoic acid (a compound where $R_2$=a hydrogen atom, n=1, and the substitution position of the carboxy group is the 3-position to the amino group, in the formula (C)), 4-aminobenzoic acid (a compound where $R_2$=a hydrogen atom, n=1, and the substitution position of the carboxy group is the 4-position to the amino group, in the formula (C)), 5-aminoisophthalic acid (a compound where $R_2$=a hydrogen atom, n=2, and the substitution position of the carboxy group is the 3-position and the 5-position to the amino group, in the formula (C)), 2-amino-4-hydroxybenzoic acid (a compound where $R_2$=hydroxy, n=1, the substitution position of the amino group is the 2-position to the carboxy group, and similarly the substitution position of the hydroxy group is the 5-position, in the formula (C)), 4-amino-5-nitrobenzoic acid (a compound where $R_2$=nitro, n=1, the substitution position of the amino group is the 2-position to the carboxy group, and similarly the substitution position of the nitro group is the 5-position, in the formula (C)), and the like.

In addition, a material compound corresponding to the group A in the formula (1) includes the following compounds.

A compound for the hydroxide ion includes alkali metal hydroxide, for example, sodium hydroxide and the like, and a compound for the amino group or the morpholino group can include respectively ammonia or morpholine.

The aliphatic amine which may have a substituent, preferably C1 to C4 alkylamine substituted by a group selected from the group consisting of a sulfo group, a carboxy group and a hydroxy group as a substituent includes 2-sulfoethylamine(taurine), carboxymethylamine(glycine), 2-hydroxyethylamine, 2-carboxyethylamine, 1-carboxyethylamine, 1,2-dicarboxyethylamine, di(carboxymethyl)amine and the like.

The aromatic amine which may have a substituent includes anilines which may be substituted, for example, by a carboxy group or a sulfo group as a substituent, and its specific examples include aniline, 3,5-dicarboxyaniline(5-aminoisophthalic acid), 4-sulfoaniline and the like.

The phenol which may have a substituent includes phenol, 4-sulfophenol, 4-carboxyphenol, 4-acetylaminophenol, 4-hydroxyphenol and the like.

The alcohol which may have a substituent includes C1 to C4 alcohol which may have a hydroxy group or a carboxy group as a substituent, and its specific examples include methoxyethanol, ethylene glycol, 3-carboxypropanol and the like.

The above compounds of the formula (A) and the formula (C) cited as the specific examples and a material compound corresponding to the group A can be appropriately combined and production can be performed according to the above, to obtain a water-soluble azo compound in Table 1 described later.

[KA 6]

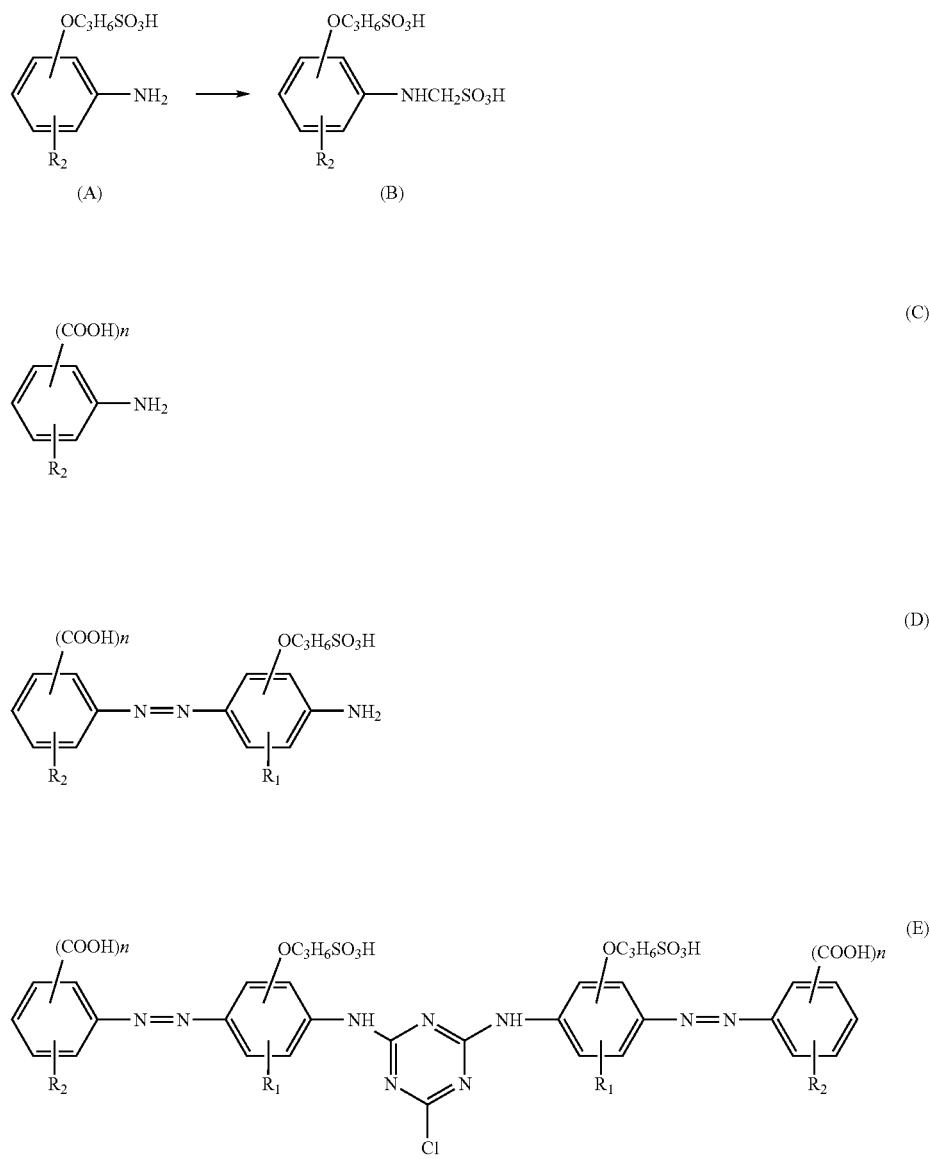

(wherein, n, $R_1$ and $R_2$ have the same meanings as in the above formula (1))

Next, specific examples of the water-soluble azo compound represented by the formula (1) of the present invention are shown in Table 1 on the basis of the following formula (6). In the formula (6), n represents 1 or 2, $R_1$ represents a hydrogen atom or a C1 to C4 alkyl group, $R_2$ represents a hydrogen atom, a nitro group or a hydroxy group, and A represents a hydroxy group, a morpholino group, a C1 to C4 alkylamino group having a hydroxy group, a sulfo group or a carboxy group as a substituent, and a mono- or di-carboxy-substituted anilino group, a phenoxy group or an amino group. A preferable group for $R_1$ and $R_2$ is a hydrogen atom, and a preferable group for A is a C1 to C4 alkylamino group having a hydroxy group, a sulfo group or a carboxy group as a substituent, more preferably a C1 to C4 alkylamino group having a sulfo group or a carboxy group, and particularly preferably a carboxymethylamino group or a sulfoethylamino group.

In addition, (COOH)n is preferably at the 3-position or the 4-position, more preferably at the 3-position, when n is 1; and at the 3-position and the 5-position when n is 2.

In Table 1, the sulfo group, the carboxy group and the hydroxy group are shown in the free acid form.

TABLE 1

Examples of the compounds

[KA 7]                                                                                                       (6)

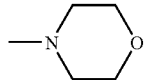

| Comp. No. | n | —COOH Pos. | $R_2$ Sub. | $R_2$ Pos. | $R_1$ Sub. | $R_1$ Pos. | A |
|---|---|---|---|---|---|---|---|
| 1 | 2 | 3.5 | H | — | H | — | —NHC$_2$H$_4$SO$_3$H |
| 2 | 2 | 3.5 | H | — | H | — | —NHCH$_2$COOH |
| 3 | 2 | 3.5 | H | — | H | — | —OH |
| 4 | 2 | 3.5 | H | — | H | — | 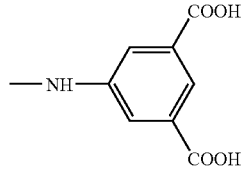 |
| 5 | 2 | 3.5 | H | — | H | — | —NHC$_2$H$_4$OH |
| 6 | 2 | 3.5 | H | — | H | — | 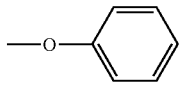 |
| 7 | 1 | 3 | H | — | H | — | —NHC$_2$H$_4$SO$_3$H |
| 8 | 1 | 3 | H | — | H | — | —OH |
| 9 | 1 | 3 | H | — | H | — | 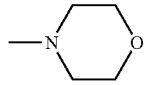 |
| 10 | 1 | 3 | H | — | CH$_3$ | 5 | —NHC$_2$H$_4$SO$_3$H |
| 11 | 1 | 4 | H | — | H | — | —NHC$_2$H$_4$SO$_3$H |
| 12 | 1 | 3 | H | — | H | — | (morpholino) |
| 13 | 1 | 3 | H | — | H | — | —NH$_2$ |
| 14 | 1 | 2 | H | — | H | — | —NHC$_2$H$_4$SO$_3$H |
| 15 | 1 | 2 | NO$_2$ | 4 | H | — | —NHC$_2$H$_4$SO$_3$H |
| 16 | 1 | 3 | OH | 4 | H | — | —NHC$_2$H$_4$SO$_3$H |
| 17 | 1 | 4 | H | — | H | — | —NHCH$_2$COOH |

(Note)
Comp. No.: Compound Number.
Pos.: Position
Sub.: Substituent

The water-soluble azo compounds of the present invention are useful as a yellow coloring matter and suitable for dyeing natural and synthetic textiles or blended fabrics, and further, these compounds are suitable for manufacturing ink for writing tools and ink compositions for inkjet recording.

When the water-soluble azo compound of the present invention is used as a yellow coloring matter, typically it can be used as a composition where additives (including a solvent and the like) to be used for dyeing are at a rate of 0 to 99.5% and the rest is said water-soluble azo compound.

Reaction solutions containing the water-soluble azo compound of the formula (1) of the present invention (for example, the reaction solution prior to pouring methanol in Example 1 described later and the like) can be used directly for manufacturing the ink composition of the present invention. However, said compound can be also isolated from the reaction solution, dried, for example spray-dried, and then processed into an ink composition. The ink composition of the present invention contains typically 0.1 to 20 mass %, more preferably 1 to 15 mass %, further preferably 2 to 10 mass % of the water-soluble azo compound of the formula (1) in an aqueous solution. The rest consists of additives for ink. For the additives for ink, all the additives other than said azo compound are included, such as water, a water-soluble organic solvent, ink preparation agents and the like. Typically, in the ink composition of the present invention, typically 0 to 30 mass % of the following water-soluble organic solvent and similarly typically 0 to 10 mass % of the ink preparation agent are contained, and the rest is water. The pH of the ink composition of the present invention is preferably 7 to 11, and more preferably 7 to 9. The ink composition whose pH is adjusted to 7 to 9 with ammonia water is more preferably.

The water-soluble azo compound of the formula (1) to be used for preparation of an ink composition preferably has less content of inorganic substances such as a metal cation chloride and sulfate, and the whole content of, for example, a sodium chloride and a sodium sulfate is approximately not more than 1 mass % in a coloring matter only as a guide for the content. In order to produce a coloring matter having less inorganic substance, a solution of the bulk powder of a coloring matter may be subjected to desalting treatment by means of a known method per se, for example, using a reverse osmosis membrane and the like.

Specific examples of the water-soluble organic solvent which can be used for the ink composition of the present invention include, for example, C1 to C4 alkanol such as methanol, ethanol, n-propanol, isopropanol, n-butanol, isobutanol, secondary butanol or tertiary butanol; carboxylic acid amide such as N,N-dimethylformamide or N,N-dimethylacetoamide; lactam such as 2-pyrrolidone or N-methyl-2-pyrrolidone; cyclic ureas such as 1,3-dimethylimidazolidin-2-one or 1,3-dimethylhexahydropyrimid-2-one; ketone or keto alcohol such as acetone, methylethylketone or 2-methyl-2-hydroxypentan-4-one; cyclic ethers such as tetrahydrofuran or dioxane; monomer, oligomer or polyalkylene glycol or thioglycol having a (C2 to C6) alkylene unit such as ethylene glycol, 1,2- or 1,3-propyleneglycol, 1,2- or 1,4-butyleneglycol, 1,6-hexylene glycol, diethylene glycol, triethylene glycol, tetraethylene glycol, dipropylene glycol, thiodiglycol, polyethylene glycol or polypropylene glycol; polyol (triol) such as glycerine or hexane-1,2,6-triol; a (C1 to C4) alkyl ether of polyhydric alcohol such as ethylene glycol monomethyl ether or ethylene glycol monoethyl ether, diethylene glycol monomethyl ether or diethylene glycol monoethyl ether or diethylene glycol monobutyl ether (butylcarbitol) or triethylene glycol monomethyl ether or triethylene glycol monoethyl ether; gamma-butyrolactone, dimethylsulfoxide and the like. These water-soluble organic solvents are used alone or in mixture. Among them, preferable are 2-pyrrolidone, N-methyl-2-pyrrolidone, mono-, di- or tri-ethylene glycol, dipropylene glycol, and more preferably 2-pyrrolidone, N-methyl-2-pyrrolidone and diethylene glycol.

In preparation of the ink composition of the present invention, the ink preparation agents which can be used according to need include, for example, an antiseptic and fungicide, a pH modifier, a chelating agent, a rust-preventive agent, a water-soluble UV absorbing agent, a water-soluble polymer compound, a dye dissolving agent, a surfactant and the like.

Examples of the antiseptic and fungicide which can be used include, for example, organic sulfur compounds, organic nitrogen sulfur compounds, organic halide compounds, haloallylsulfone compounds, iodopropargyl compounds, N-haloalkylthio compounds, nitrile compounds, pyridine compounds, 8-oxyquinoline compounds, benzothiazole compounds, isothiazoline compounds, dithiol compounds, pyridine oxide compounds, nitropropane compounds, organic tin compounds, phenol compounds, quaternary ammonium salt compounds, triazine compounds, thiadiazine compounds, anilide compounds, adamantane compounds, dithiocarbamate compounds, brominated indanone compounds, benzyl bromoacetate compounds and inorganic salt compounds. The organic halide compound includes, for example, sodium pentachlorophenol; the pyridine oxide compound includes, for example, sodium 2-pyridinethiol-1-oxide; the isothiazoline compound includes, for example, 1,2-benzisothiazolin-3-one, 2-n-octyl-4-isothiazolin-3-one, 5-chloro-2-methyl-4-isothiazolin-3-one, 5-chloro-2-methyl-4-isothiazolin-3-one magnesium chloride, 5-chloro-2-methyl-4-isothiazolin-3-one calcium chloride, 2-methyl-4-isothiazolin-3-one calcium chloride and the like; respectively. Other antiseptic and fungicides include sodium sorbate, sodium benzoate and the like.

As the pH modifier, any substance can be used as long as it can control the pH of the ink typically in the range of 7.0 to 11.0 without any adverse effects on the ink composition to be prepared. Specific examples of the pH modifier which can be used include, for example, alkanolamines such as diethanolamine and triethanolamine, hydroxides of alkali metal such as lithium hydroxide, sodium hydroxide and potassium hydroxide, ammonium hydroxide, carbonates of alkali metal such as lithium carbonate, sodium carbonate and potassium carbonate, and the like.

Examples of the chelating agent which can be used include, for example, sodium ethylenediamine tetraacetate, sodium nitrilotriacetate, sodium hydroxyethylethylenediamine triacetate, sodium diethylenetriamine pentaacetate, sodium uracil diacetate and the like. The rust-preventive agent which can be used includes, for example, acidic sulfite salt, sodium thiosulfate, ammonium thioglycolate, diisopropylammonium nitrite, pentaerythritol tetranitrate, dicyclohexylammonium nitrite and the like.

Examples of the water-soluble UV absorbing agent which can be used include, for example, sulfonated benzophenone, sulfonated benzotriazole and the like.

Examples of the water-soluble polymer compound which can be used include, for example, polyvinyl alcohol, cellulose derivatives, polyamines, polyimines and the like.

Examples of the dye dissolving agent which can be used include, for example urea, ε-caprolactam, ethylene carbonate and the like.

Examples of the surfactant which can be used include, for example, anionic surfactants, amphoteric surfactants, cationic surfactants, nonionic surfactants and the like. Further, the anionic surfactant includes alkyl sulfocarboxylate, alphaolefin sulfonate, polyoxyethylene alkyl etheracetate, n-acylamino acid and a salt thereof, an n-acylmethyltaurine salt, rosin acid soap, castor oil sulfate, lauryl alcohol sulfate, alkylphenol phosphate, alkyl phosphate, alkylallylsulfonate, diethyl sulfosuccinate, diethylhexyl sulfosuccinate, dioctyl sulfosuccinate and the like. And the cationic surfactant includes 2-vinylpyridine derivatives, poly4-vinyl pyridine derivatives and the like.

Furthermore, the amphoteric surfactant includes, for example, lauryldimethylaminoacetic acid betaine, 2-alkyl-N-carboxymethyl-N-hydroxyethylimidazolinium betaine, coconut oil fatty acid amide propyldimethylaminoacetic acid betaine, polyoctylpolyaminoethylglycine, imidazoline derivatives and the like. In addition, the nonionic surfactant includes ethers such as polyoxyethylene nonylphenyl ether, polyoxyethylene octylphenyl ether, polyoxyethylene dodecylphenyl ether, polyoxyalkylene alkyl ether such as polyoxyethylene oleyl ether, polyoxyethylene lauryl ether and polyoxyethylene alkyl ether; polyoxyethylene oleic acid; esters such as polyoxyethylene oleic acid ester, polyoxyethylene distearate, sorbitan laurate, sorbitan monostearate, sorbitan monooleate, sorbitan sesquioleate, polyoxyethylene monooleate and polyoxyethylene stearate; acetylene glycols such as 2,4,7,9-tetramethyl-5-decyne-4,7-diol, 3,6-dimethyl-4-octyne-3,6-diol and 3,5-dimethyl-1-hexine-3-ol (for example, Surfynol 104, 104PG50, 82, 465, Olfine STG and the like, manufactured by Nissin Chemical Industry Co., Ltd.), and the like.

These ink preparation agents are used alone or in mixture, respectively.

The ink composition of the present invention can be produced by dissolving a water-soluble azo compound represented by the formula (1) in water, if necessary, together with a water-soluble organic solvent, the above ink preparation agents and the like. When a reaction solution containing a water-soluble azo compound of the formula (1) is directly used for producing an ink composition, it has preferably a less content of inorganic substances such as chlorides of metal cation, sulfate and the like, and the content is, only as a guide, approximately not more than 1 mass % per a bulk powder of coloring matter contained in the reaction solution as described above. In order to produce a coloring matter with less inorganic substance, the reaction solution can be subjected to desalting treatment, for example, by a known method per se using a reverse osmosis membrane, and the like.

The order to dissolve the ingredients in the above producing method is not particularly limited. A water-soluble azo compound represented by the formula (1) may be dissolved in water and/or a water-soluble organic solvent in advance, and then ink preparation agents may be added and dissolved therein; or a water-soluble azo compound represented by the formula (1) may be dissolved in water, and then a water-soluble organic solvent and ink preparation agents may be added and dissolved therein. The order may be different from this, and a water-soluble organic solvent and ink preparation agents are added to a reaction solution of a water-soluble azo compound represented by the formula (1) or a liquid subjected to desalting treatment thereof using a reverse osmosis membrane, to produce the ink composition. Water to be used for preparation of the ink composition of the present invention has preferably less impurities, such as ion-exchanged water or distilled water. In addition, after preparing the ink composition, foreign substances may be removed by carrying out microfiltration, if necessary, using membrane filters and the like, and microfiltration is preferably carried out particularly in the case of using the ink composition as an ink composition for an ink jet printer. The pore size of a filter to be used for carrying out microfiltration is typically 1 micron to 0.1 micron, and preferably 0.8 microns to 0.2 microns.

The ink composition of the present invention is suitable for impress printing, copying, marking, writing, drafting, stamping, recording (printing) and the like, especially for use in inkjet recording. In these cases, high quality yellow-printed articles which have good fastnesses against water, sun light, ozone and friction are provided.

The colored article of the present invention is an article colored with the compound of the present invention. The materials to be colored are not limited, for example, including paper, textile or cloth (cellulose, nylon, wool and the like), leather, substrates for color filters and the like, but not limited thereto. The coloring method includes, for example, printing methods such as dip dyeing, textile printing, screen printing, methods by ink jet printers and the like, and preferably methods by ink jet printers.

There is an ink jet printer where two kinds of inks of the same color, a high concentration ink and a low concentration ink, are loaded for the purpose of supplying high resolution images. In that case, an ink composition with a high concentration and an ink composition with a low concentration may be manufactured respectively using a water-soluble azo compound represented by the formula (1) of the present invention, and then they can be used for an ink set. Otherwise, the ink composition containing a water-soluble azo compound represented by the formula (1) may be used for either of the inks. Further, the water-soluble azo compound represented by the formula (1) of the present invention and a known yellow coloring matter may be used in combination. The water-soluble azo compound represented by the formula (1) can be used for adjusting the hue of another color, for example, black ink or for the purpose of preparing a red ink or a green ink by mixing with a magenta coloring matter or a cyan coloring matter.

Record-receiving materials (medium) on which the inkjet recording method of the present invention can be applied include, for example, plain paper, communication sheet, textile, leather and the like. Among them, the communication sheet is preferably subjected to surface treatment, specifically provided with an ink receiving layer on the substrate of paper, film or the like. The ink receiving layer can be provided, for example, by impregnating or coating a cation polymer on these substrate, or by coating, on the surface of the above substrates, a porous white inorganic substance which can absorb coloring matter in the ink, such as porous silica, aluminasol or special ceramics, together with a hydrophilic polymer such as polyvinyl alcohol or polyvinylpyrrolidone. Such paper as provided with an ink receiving layer is typically called inkjet professional paper (film) or glossy paper (film), and commercially available, for example, under the names of Pictorico (trade name, manufactured by Asahi Glass Co., Ltd.), Professional Photopaper, Super Photopaper, Matte Photopaper (trade names, all are manufactured by Canon Inc.), Photo Paper (Glossy), Photo Matte Paper and Super Fine Glossy Film (trade names, all are manufactured by SEIKO-EPSON CORPORATION), Premium Plus Photo Paper, Premium Glossy Film and Photo Paper (trade names, all are manufactured by Hewlett Packard Japan, Ltd.), PhotoLikeQP (trade name, manufactured by KONIKA Corporation) and the like.

Among them, it is known that ozone gas develops discoloration or fading of coloring matters of images recorded particularly on a record-receiving material coated with a porous white inorganic substance on the surface, but the ink composition of the present invention imparts superior recorded images with less discoloration or fading in the case of recording on such record-receiving materials, due to its excellent gas fastness.

In order that recording is performed on a record-receiving material by the inkjet recording method of the present invention, for example, a container filled with the above ink composition is loaded in the predefined position of an inkjet printer to record on a record-receiving material in a general manner.

In the inkjet recording method of the present invention, the yellow ink composition of the present invention can be used in combination with a magenta ink composition, a cyan ink composition, if necessary, a green ink composition, a blue (or violet) ink composition, a red ink composition, a black ink composition and the like. In this case, each of the color ink compositions is filled into each of the containers, and then the containers are loaded in the predefined positions of an ink jet printer for use. Examples of the ink jet printer which can be used include printers, for example, a piezo inkjet printer utilizing mechanical vibration and a bubble-jet printer (registered trademark) utilizing bubbles generated by heating, and the like.

The ink composition of the present invention exhibits vivid yellow and has high color definition particularly on professional paper or glossy paper for inkjet and suitable hue for the inkjet recording method. In addition, it is characterized by very high fastness of the recorded images. The ink composition of the present invention does not precipitate nor separate during storage. Further, the ink composition of the present invention does not cause clogging of injectors (ink heads) when used for inkjet recording. The ink composition of the present invention exhibits no change in its physical property under recirculation for a relatively long period of time by a continuous inkjet printer or in intermittent use by an on-demand inkjet printer.

Hereinafter, the present invention will be further specifically explained by Examples. In this connection, "parts" and "%" in Examples are based on mass unless otherwise specifically noted.

And each λmax of the synthesized compounds is shown as the measured value in an aqueous solution of pH 7 to 8. In addition, the obtained compounds of the formulas (7) to (10) are shown in the free acid form for convenience, but in the following examples, each compound of the formulas (7) to (10) was obtained as a mixture salt of free acid and a sodium salt.

EXAMPLE 1

While adjusting the pH to 6 with a sodium hydroxide, 36.2 parts of 5-aminoisophthalic acid was dissolved in 210 parts of water, and 14.8 parts of sodium nitrite was added thereto. This solution was added dropwise in 510 parts of 5% hydrochloric acid of 5 to 10° C. over 30 minutes, and then stirred at no more than 10° C. for 1 hour to carry out diazotization reaction. Next, 46.2 parts of 2-sulfopropoxyanilines was dissolved in 130 parts of water, while adjusting the pH to 5 with a sodium hydroxide, to make methyl-ω-sulfonic acid derivatives in a conventional manner using 21.8 parts of sodium bisulfite and 18.0 parts of 35% formalin, which derivatives were then charged into the above synthesized diazonium salt and stirred at 0 to 5° C. and pH 0 to 2 for 2 hours. The reaction solution was adjusted to pH 11 with a sodium hydroxide and then stirred at 65 to 70° C. for 5 hours while maintaining the same pH value, and further subjected to salting out with 240 parts of a sodium chloride to obtain 160 parts of an azo compound having an amino group as a wet cake. Next, 0.14 parts of LEOCOL TD90 (surfactant, manufactured by Lion Corporation) was added in 250 parts of ice water and stirred violently, and 13.8 parts of a cyanuric chloride was added therein and stirred at 0 to 5° C. for 30 minutes. Subsequently, this suspension was added dropwise, over 30 minutes, into the solution which had been obtained with 160 parts of the above obtained azo compound having an amino group as a wet cake and 400 parts of water. After completion of the dropwise addition, it was stirred at pH 5 to 6 at 20 to 25° C. for 2 hours, and then 11.2 parts of taurine was charged thereto and stirred at pH 7 to 8 at 75 to 80° C. for 3 hours. After the resulting reaction solution was cooled to 20 to 25° C., 800 parts of methanol was charged into this reaction solution and stirred at 20 to 25° C. for 1 hour followed by filtration to obtain 95.0 parts of a wet cake. This wet cake was dried by a hot air dryer (80° C.) to obtain 56.0 parts of a water-soluble azo compound (λmax 390 nm) of the present invention represented by the following formula (7).

[KA 8]

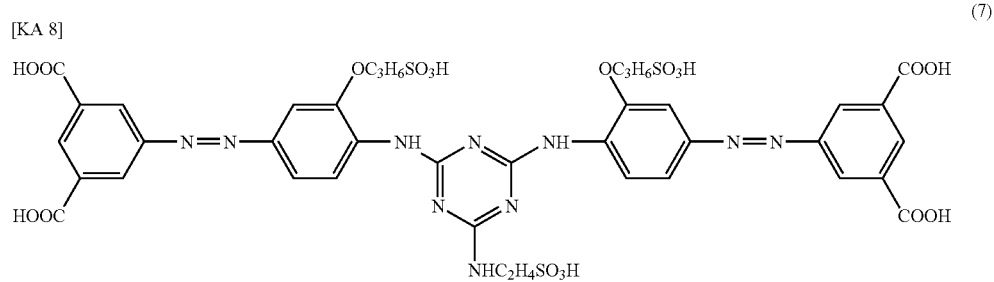

(7)

EXAMPLE 2

In the same manner as in Example 1 except that 6.8 parts of glycine was used instead of 11.2 parts of taurine in Example 1, 52.0 parts of a water-soluble azo compound (λmax 393 nm) represented by the following formula (8) of the present invention was obtained.

[KA 9]

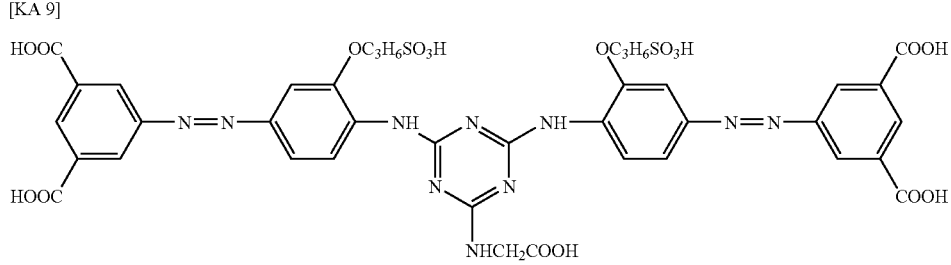

(8)

EXAMPLE 3

In the same manner as in Example 1 except that 27.4 parts of 3-aminobenzoic acid was used instead of 36.2 parts of 5-aminoisophthalic acid in Example 1, 50.0 parts of a water-soluble azo compound (λmax 383 nm) of the present invention represented by the formula (9) of the present invention was obtained.

In addition, 4-aminobenzoic acid can be used instead of 3-aminobenzoic acid in the present example to obtain a compound of Compound No. 11 in Table 1.

above synthesized diazonium salt was charged thereto and stirred at 10 to 15° C. and pH 5 to 6 for 3 hours. The reaction solution was adjusted to pH 12 with a sodium hydroxide and then stirred at 80 to 90° C. for 2 hours. The resulting reaction solution was filtered, and then the filtrate was completely dried by a hot air dryer (80° C.) to obtain 40.1 parts of an azo compound containing an amino group. Next, 9.3 parts of cyanuric chloride was stirred violently and suspended in 200 parts of ice water, and 40.1 parts of the azo compound containing an amino group dissolved in 400 parts of water was added dropwise thereto over 1 hour. After the dropwise addi-

[KA 10]

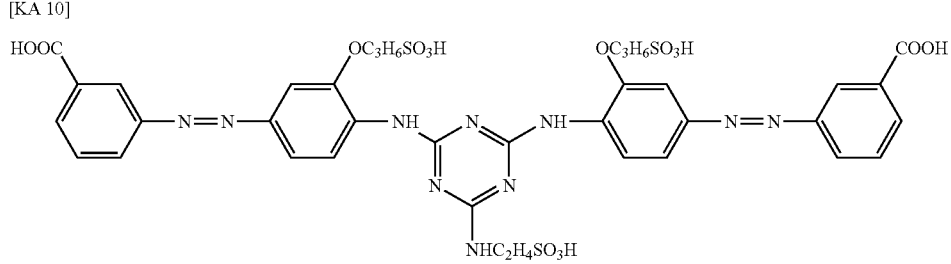

(9)

EXAMPLE 4

While adjusting the pH to 6 with a sodium hydroxide, 18.1 parts of 5-aminoisophthalic acid was dissolved in 100 parts of water, and 7.2 parts of sodium nitrite was added thereto. This solution was added dropwise in 255 parts of 5% hydrochloric acid of 5 to 10° C. over 1 hour, and then stirred at no more than 10° C. for 1 hour to carry out diazotization reaction. Next, 23.1 parts of 2-sulfopropoxyaniline was dissolved in 70 parts of water, while adjusting the pH to 5 with a sodium hydroxide, to make methyl-ω-sulfonic acid derivatives in a conventional manner using sodium bisulfite and formalin, and then the tion, it was stirred at pH 3 to 3.5 at 5 to 10° C. for 1 hour, and subsequently at pH 5 to 6 at 30 to 40° C. for 3 hours, and then stirred at pH 9 to 10 at 80 to 90° C. for 4 hours. The resulting reaction solution was filtered and then the filtrate completely dried by a hot air dryer (80° C.) to obtain 54.0 parts of coloring matter powder. This coloring matter powder was charged into 300 parts of water and 700 parts of methanol and stirred for 1 hour, and then separated by filtration. The obtained wet cake was completely dried by a hot air dryer (80° C.) to obtain 45.0 parts of a compound (λmax 383 nm) represented by the following formula (10).

[KA 11]

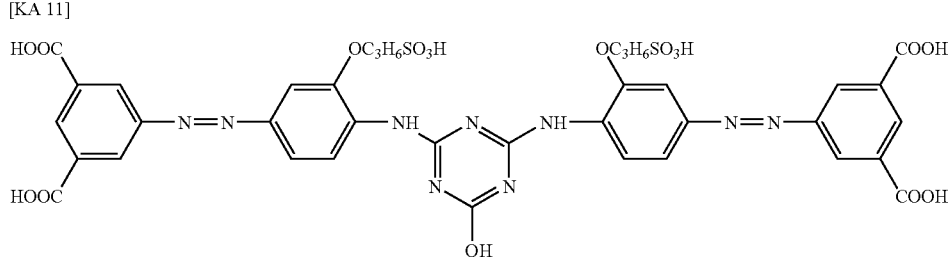

(10)

EXAMPLES 5 TO 8

(A) Preparation of Ink

Each of the azo compounds of the present invention obtained in the above Examples 1, 2, 3 and 4 was mixed at the composition ratio shown in Table 2 to obtain each of the ink compositions of the present invention, and foreign substances were removed therefrom respectively by filtration with a 0.45 μm membrane filter. In this connection, ion-exchanged water was used as water and the pH of the ink composition was adjusted at pH=7 to 9 with 28% ammonia water, and then water was added thereto so that the total amount was 100 parts. The ink compositions obtained by using the azo compounds obtained in Example 1 (the compound of the formula (7): Compound No. 1), Example 2 (the compound of the formula (8): Compound No. 2), Example 3 (the compound of the formula (9): Compound No. 7) and Example 4 (the compound of the formula (10): Compound No. 3) are respectively for Example 5, Example 6, Example 7 and Example 8.

TABLE 2

(Composition ratio of ink composition)

| | |
|---|---|
| Each azo compound obtained in Example 1 to Example 4 | 5.0 parts |
| Glycerine | 5.0 parts |
| Urea | 5.0 parts |
| N-methyl-2-pyrrolidone | 4.0 parts |
| Isopropyl alcohol | 3.0 parts |
| Butyl carbitol | 2.0 parts |
| Surfynol 104PG50 (see the note below) | 0.1 part |
| 28% ammonia water + water | 75.9 parts |
| Total | 100.0 parts |

(Note)
Trade name: an acetylene glycol nonionic surfactant, manufactured by Nissin Chemical Industry Co., Ltd.

As a control for comparison, an ink composition for comparison was prepared at the composition ratio of Table 3 using C.I. Direct Yellow 132 which is widely used as a yellow coloring matter for inkjet (Comparative Example 1).

TABLE 3

(Composition ratio of ink composition for comparison)

| | |
|---|---|
| C.I. Direct Yellow 132 | 3.0 parts |
| Glycerine | 5.0 parts |
| Urea | 5.0 parts |
| N-methyl-2-pyrrolidone | 4.0 parts |
| Isopropyl alcohol | 3.0 parts |
| Butyl carbitol | 2.0 parts |

TABLE 3-continued (Composition ratio of ink composition for comparison)

| | |
|---|---|
| Surfynol 104PG50 (see the above note) | 0.1 part |
| 28% ammonia water + water | 77.9 parts |
| Total | 100.0 parts |

(B) Inkjet Printing

Using an ink jet printer (trade name: Pixus 860i, manufactured by Canon Inc.), inkjet recording was performed on two kinds of paper, glossy paper 1 (trade name: Professional Photopaper PR-101, manufactured by Canon Inc.) and glossy paper 2 (trade name: Photo Paper (Glossy) KA450PSK, manufactured by SEIKO-EPSON CORPORATION), having an ink receiving layer containing a porous white inorganic substance. In inkjet recording, such an image pattern was made that several gradations of reflection density can be obtained and yellow printed samples were obtained.

Moisture fastness test was carried out using a print having unprinted part and printed part, and in light fastness test and ozone gas fastness test, measurement of reflection density was carried out on the part of a printed sample which had had the reflection density D value nearest to 1 before the test. In this connection, reflection density was measured using a calorimetric system "GRETAG SPM50" (trade name, manufactured by Gretag Macbeth AG).

(C) Moisture Fastness Test for Recorded Image

The test pieces printed on glossy paper 1 and glossy paper 2 were left at 50° C. and 90% RH (relative humidity) for 7 days by using a thermo-hygrostat (manufactured by Ohken Co., Ltd) and bleeding of the coloring matter (dye) from the printed part to the unprinted part is judged by visual observation before and after the test. The results are shown in Table 4. The evaluation criteria are as follows.
- ○ Bleeding of the coloring matter to the unprinted part is hardly observed.
- Δ Bleeding of the coloring matter to the unprinted part is slightly observed.
- x Bleeding of the coloring matter to the unprinted part is largely observed.

(D) Xenon Light Fastness Test of Recorded Image

The test pieces printed on glossy paper 1 and glossy paper 2 were placed on the holder together with a glass plate having a thickness of 2 mm through an air layer between them and irradiated at an illuminance of 0.36 W/m$^2$ for 50 hours, using a xenon weatherometer Ci4000 (trade name, manufactured by ATRAS Electric Devices Co.). After the test, reflection density was measured using the calorimetric system. After the measurement, residual rate of the coloring matter were calculated by (reflection density after the test/reflection density before the test)×100(%) to evaluate according to 3 scales.

Residual rate of coloring matter is not less than 85% . . . ○
Residual rate of coloring matter is not less than 75% and less than 85% . . . Δ
Residual rate of coloring matter is less than 75% . . . x The results are shown in Table 4.

(E) Ozone Gas Fastness Test of Recorded Image

The test pieces printed on glossy paper 1 and glossy paper 2 were left for 3 hours under the circumstances of an ozone concentration of 40 ppm, a humidity of 60% RH and a temperature of 24° C., using an ozone weatherometer (manufactured by Suga Test Instruments Co., Ltd.), and then reflection density is measured using the above calorimetric system. After the measurement, residual rate of the coloring matters were calculated by (reflection density after the test/reflection density before the test)×100(%) to evaluate according to 3 scales.

Residual rate of coloring matter is not less than 65% . . . ○
Residual rate of coloring matter is not less than 55% and less than 65% . . . Δ
Residual rate of coloring matter is less than 55% . . . x The results are shown in Table 4.

(F) Solubility Test

On the azo compounds used for the ink compositions of Examples 5 to 8 (each azo compound (Na salt) obtained in Example 1 to Example 4), solubility to water was tested. Ion-exchanged water was used as water, and the test was carried out around pH 8 and at room temperature (about 25° C.). Solubility was evaluated according to the following evaluation criteria.

Solubility is high compared with C.I. Direct Yellow 132 . . . ○
Solubility is equivalent to C.I. Direct Yellow 132 . . . Δ
Solubility is low compared with C.I. Direct Yellow 132 . . . x The results are shown in the sections of Examples 5 (the azo compound of Example 1), 6 (the azo compound of Example 2), 7 (the azo compound of Example 3) and 8 (the azo compound of Example 4) of Table 4.

TABLE 4

| | The results of the tests | | | |
|---|---|---|---|---|
| | Solubility | Moisture fastness | Ozone gas fastness | Light fastness |
| Example 5 | ○ | | | |
| (Glossy paper 1) | | ○ | ○ | ○ |
| (Glossy paper 2) | | ○ | ○ | ○ |
| Example 6 | ○ | | | |
| (Glossy paper 1) | | ○ | ○ | ○ |
| (Glossy paper 2) | | ○ | ○ | ○ |
| Example 7 | ○ | | | |
| (Glossy paper 1) | | ○ | ○ | ○ |
| (Glossy paper 2) | | ○ | ○ | ○ |
| Example 8 | ○ | | | |
| (Glossy paper 1) | | ○ | ○ | ○ |
| (Glossy paper 2) | | ○ | ○ | ○ |
| Comparative Example 1 | — | | | |
| (Glossy paper 1) | | ○ | Δ | Δ |
| (Glossy paper 2) | | x | ○ | ○ |

As is clear from the results of Table 4, the compound of Comparative Example 1 (C.I. Direct Yellow 132) has a residual rate of coloring matter in the range of no less than 55% and less than 65% in the ozone gas fastness test using glossy paper 1, and also in the range of no less than 75% and less than 85% in the light fastness test, resulting in that it has a problem in terms of these fastnesses. Further, bleeding of coloring matter to the unprinted part was largely observed in the moisture fastness test using glossy paper 2, so it also has a problem in terms of moisture fastness. Compared with this, for each ink compositions of Example 5 to Example 8 (the ink composition of the present invention), even when any of the glossy papers was used, the residual rate of coloring matter was no less than 65% in the ozone gas fastness test and no less than 85% in the light fastness test, and bleeding of coloring matter to the unprinted part was hardly observed in the moisture fastness test, showing high fastnesses in all the tests. In addition, they also showed results exceeding the compound of Comparative Example 1 in the solubility test.

Judging from the above results, it is clear that the water-soluble azo compound of the present invention is a compound suitable for preparing ink compositions particularly for inkjet recording and very useful as a yellow coloring matter for inkjet ink.

INDUSTRIAL APPLICABILITY

The water-soluble azo compound of the present invention is useful as a yellow coloring matter, highly water-soluble, and suitable for ink compositions; the obtained ink composition has good storage stability and does not precipitate nor separate during storage, nor change in quality in use for a long time by an ink jet printer, nor clog an injector (ink head); the articles colored with said azo compound, particularly colored articles by printing on professional paper for inkjet or glossy paper by an ink jet printer have high color definition and high fastnesses such as ozone fastness and the like; and the compound is very useful as a yellow coloring matter for inkjet ink.

The invention claimed is:

1. A water-soluble azo compound represented by the following-formula (1)

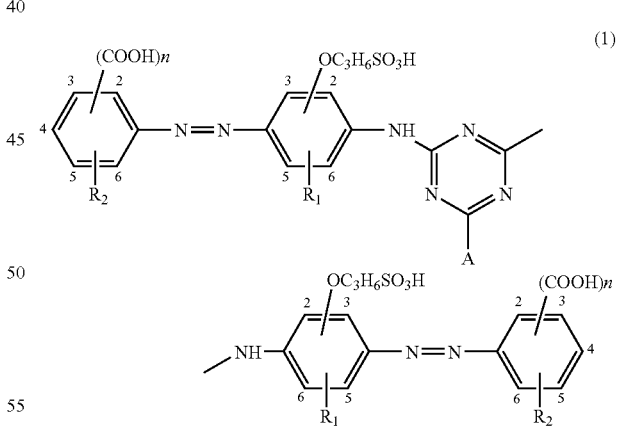

wherein, A represents a hydroxy group, an amino group, a morpholino group, an aliphatic amine residue which may have a substituent, an aromatic amine residue which may have a substituent, a phenoxy group which may have a substituent or an alkoxy group which may have a substituent, $R_1$ represents a hydrogen atom or an alkyl group having 1 to 4 carbon atoms, $R_2$ represents a hydrogen atom, a nitro group or a hydroxy group, n represents an integer number of 1 to 3, respectively as a free acid.

2. The water-soluble azo compound according to claim 1, wherein $R_1$ in the formula (1) is a hydrogen atom.

3. The water-soluble azo compound according to claim 1 or 2, wherein $R_2$ in the formula (1) is a hydrogen atom.

4. The water-soluble azo compound according to claim 1, wherein A in the formula (1) is a group represented by the following formula (2) or (3)

—NHC$_2$H$_4$SO$_3$H    (2)

—NHCH$_2$COOH    (3)

or a hydroxy group.

5. An ink composition comprising the water-soluble azo compound according to claim 1.

6. The ink composition according to claim 5, comprising a water-soluble organic solvent.

7. The ink composition according to claim 5, which is for inkjet recording.

8. An inkjet recording method comprising discharging ink droplets of an ink composition comprising the water-soluble azo compound according to claim 1 to recording signals to perform recording on a record-receiving material.

9. The inkjet recording method according to claim 8, wherein the record-receiving material is a communication sheet.

10. The inkjet recording method according to claim 9, wherein the communication sheet is a sheet having an ink receiving layer comprising a porous white inorganic substance.

11. A colored article colored with the water-soluble azo compound according to claim 1.

12. The colored article according to claim 11, wherein coloring is performed by an ink jet printer.

13. An ink jet printer loaded with a container containing the ink composition according to any one of claims 5 to 7.

14. The water-soluble azo compound according to claim 1, wherein in the formula (1), n is 1 or 2, A is a hydroxy group, an amino group, a morpholino group, a C1 to C4 alkylamino group having a hydroxy group, a sulfo group or a carboxy group as a substituent, an anilino group substituted by a mono- or di-carboxy group, or a phenoxy group, and —OC$_3$H$_6$SO$_3$H is substituted on the 3-position to the azo group.

15. The water-soluble azo compound according to claim 1, wherein (COOH)n in the formula (1) is substituted at the 3-position or the 4-position when n=1, and at the 3-position and the 5-position when n=2.

16. The water-soluble azo compound according to claim 1, wherein $R_1$ in the formula (1) is a hydrogen atom, and (COOH)n is substituted at the 3-position or the 4-position when n=1, and at the 3-position and the 5-position when n=2.

17. The water-soluble azo compound according to claim 1, wherein A in the formula (1) is a hydroxy group or a C1 to C4 alkylamino group having a sulfo group or a carboxy group as a substituent, $R_1$ is a hydrogen atom, (COOH)n is substituted at the 3-position or the 4-position when n=1, and at the 3-position and the 5-position when n=2.

18. The water-soluble azo compound according to claim 17, wherein A in the formula (1) is a sulfoethylamino group or a carboxy methylamino group, $R_2$ is a hydrogen atom, n=2 and the substitution positions of the two carboxy groups are the 3-position and the 5-position.

19. A yellow coloring matter comprising the compound of the formula (1).

* * * * *